(12) United States Patent
Wu et al.

(10) Patent No.: US 10,849,776 B2
(45) Date of Patent: Dec. 1, 2020

(54) HANDHELD DEVICE AND VIBRATION CANCELLATION METHOD

(71) Applicant: JEMPTEK Technology Inc., Taipei (TW)

(72) Inventors: Yung-Hsi Wu, Taipei (TW); Po-Chih Hung, Hsinchu County (TW)

(73) Assignee: INALWAYS CORPORATION, New Taipei (TW)

( * ) Notice: Subject to any disclaimer, the term of this patent is extended or adjusted under 35 U.S.C. 154(b) by 201 days.

(21) Appl. No.: 14/806,661

(22) Filed: Jul. 23, 2015

(65) Prior Publication Data
US 2017/0020704 A1    Jan. 26, 2017

(51) Int. Cl.
| | |
|---|---|
| *A61F 4/00* | (2006.01) |
| *A61B 5/11* | (2006.01) |
| *A61F 7/10* | (2006.01) |
| *A61B 5/00* | (2006.01) |
| *A61H 1/00* | (2006.01) |
| *A47G 21/08* | (2006.01) |
| *F16F 7/10* | (2006.01) |
| *G01P 1/00* | (2006.01) |

(52) U.S. Cl.
CPC ............... *A61F 4/00* (2013.01); *A47G 21/08* (2013.01); *A61B 5/1101* (2013.01); *A61B 5/4836* (2013.01); *A61B 5/6887* (2013.01); *A61H 1/00* (2013.01); *F16F 7/1005* (2013.01); *A47G 2200/046* (2013.01); *A47G 2200/205* (2013.01); *A61B 2562/0219* (2013.01); *A61H 2201/501* (2013.01); *A61H 2201/5097* (2013.01); *G01P 1/003* (2013.01)

(58) Field of Classification Search
CPC ........... A61F 4/00; A61B 5/1101; A61H 1/00; G02B 27/646; F16F 7/1005; G01P 1/003
See application file for complete search history.

(56) References Cited

U.S. PATENT DOCUMENTS

| | | | |
|---|---|---|---|
| 9,545,568 B2 * | 1/2017 | Grant | G06F 3/016 |
| 2001/0012932 A1 | 8/2001 | Peer | |
| 2005/0243061 A1 * | 11/2005 | Liberty | A61B 5/1171 345/158 |
| 2006/0139930 A1 * | 6/2006 | Feinsod | G02B 27/20 362/276 |
| 2010/0228362 A1 | 9/2010 | Pathak | |

(Continued)

FOREIGN PATENT DOCUMENTS

| | | |
|---|---|---|
| CN | 102722644 A | 10/2012 |
| CN | 103906483 A | 7/2014 |

(Continued)

*Primary Examiner* — Jennifer Dieterle
*Assistant Examiner* — Melissa A Hoban
(74) *Attorney, Agent, or Firm* — Winston Hsu (57) ABSTRACT

A handheld device includes a base comprising a handgrip for receiving a vibration movement, a gripping element linked to the base for releasably connecting the handheld device to an object, at least one inertia sensor for detecting an acceleration of the vibration movement to generate an acceleration signal, a processing unit for determining to generate a cancellation decision according to the acceleration signal, and at least one actuator for controlling movement of the gripping element according to the cancellation decision, such that the acceleration is counteracted.

8 Claims, 6 Drawing Sheets

(56) References Cited

U.S. PATENT DOCUMENTS

2013/0297022 A1 11/2013 Pathak
2014/0074180 A1* 3/2014 Heldman ............. A61B 5/1101
                                                     607/45
2014/0316310 A1* 10/2014 Ackermann ....... A61N 1/36046
                                                     601/46

FOREIGN PATENT DOCUMENTS

| CN | 204426918 U | 7/2015 |
|----|-------------|--------|
| JP | 200867936 A | 3/2008 |
| TW | M426397 U1 | 4/2012 |
| TW | M493704 U | 1/2015 |

* cited by examiner

HANDHELD DEVICE AND VIBRATION CANCELLATION METHOD

BACKGROUND OF THE INVENTION

1. Field of the Invention

The present invention is related to a handheld device and vibration cancellation method, and more particularly, to a handheld device and vibration cancellation method minimizing discomfort and inconvenience of a patient by counteracting tremor's movements.

2. Description of the Prior Art

Tremors refer to unintentional muscle movements in the human body. People diagnosed with neurologically caused disorders suffer from the tremors. Essential tremor is a common tremor type, and many people, elders particularly, suffer from this type of tremor. Effects of the essential tremor could cause significant disability. People diagnosed with this tremor could have troubles performing necessary daily functions, such as eating, drinking, using keys, typing on a computer, or applying make-up, causing a reduction in the quality of life for those people.

Various treatments for the essential tremor exist, but have shown limited effectiveness so far. For example, pharmacologic treatments are known to help alleviate unwanted muscle motion. However, the effectiveness of these treatments can vary and are typically prescribed on a trial-and-error basis. In addition, side effects can be significant because the beta blockers commonly used for the essential tremor mask signs of hypoglycemia and may cause memory loss and confusion in the elderly. For patients who are resistant to drug treatment or have severely disabling tremor, pharmacologic solutions alone are often inadequate. In these cases surgical treatments such as thalamic deep brain stimulation may be used. But these treatments involve operative and post-operative risks and are not always desirable.

Despite current treatment options, many patients possess tremor that is not curable or decline treatment because they consider the risks and side-effects to be unbearable. One approach for this group is the use of tremor suppression devices that physically force a person's tremor to cease. These devices are supported by a large unmoving mass and deliver an appropriately timed and measured force against the user's affected body part. For instance, physically grounded joysticks supported by a heavy table have been developed to mechanically dampen a person's tremor to aid in the overall control of electronic wheelchairs. In another example, wearable prosthetics suppress tremor using active control that are produced from the bulk of the operator's body. While physically grounded devices are capable of forcing a person's tremor to cease, the person suffers from some disadvantages, such as discomfort or pain that occurs when relatively large forces are applied to an affected limb. In addition, these devices typically cannot distinguish between intended and unintended motions. Therefore, patients encounter resistance to all regular directed movements masking the experience of wearing the device awkward and obtrusive. Furthermore, most grounded prosthetics require a complex structure, adding to overall size, weight, and cost, which can render the grounded prosthetics impractical for use in daily activities.

Furthermore, shape memory alloy (SMA) is employed to control movements of these tremor suppression devices. However, SMA has a metal fatigue problem, which will get more and more serious as time goes by and finally disable these tremor suppression devices.

Therefore, the conventional tremor suppression devices have to be improved.

SUMMARY OF THE INVENTION

Therefore, one of the objectives of the present invention is to provide a handheld device and a vibration cancellation method.

The present invention discloses a handheld device comprising a base comprising a handgrip for receiving a vibration movement, a gripping element linked to the base for releasably connecting the handheld device to an object, at least one inertia sensor for detecting an acceleration of the vibration movement to generate an acceleration signal, a processing unit for determining to generate a cancellation decision according to the acceleration signal, and at least one actuator for controlling movement of the gripping element according to the cancellation decision, such that the acceleration is counteracted.

The present invention further discloses a vibration cancellation method for controlling a gripping element, comprising detecting an acceleration of a vibration movement, rejecting frequency components of the acceleration outside a frequency range, removing the gravity component from the acceleration, lifting up the gripping element if the acceleration is less than a first threshold, and lowering down the gripping element if the acceleration is greater than a second threshold.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
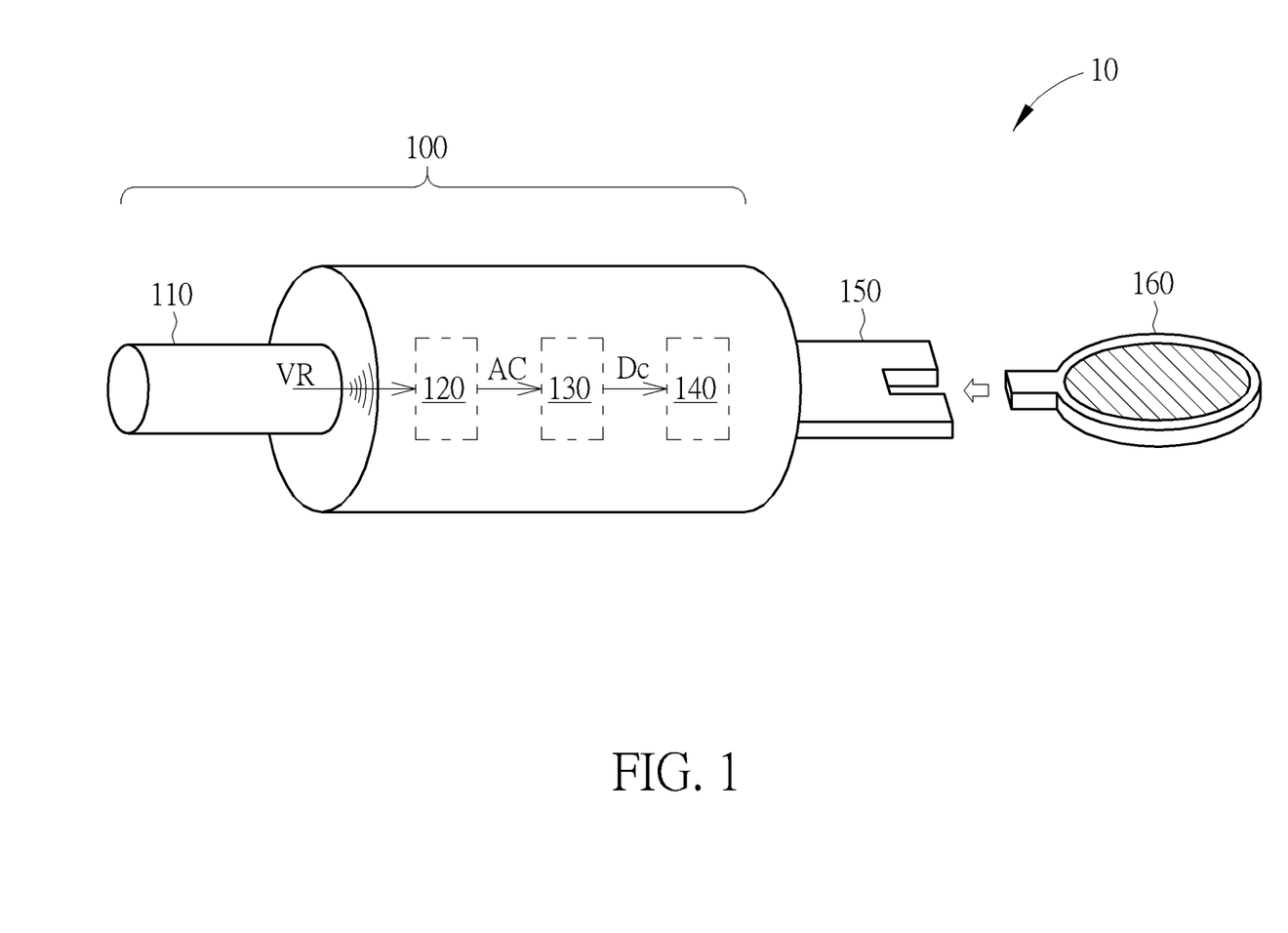
FIG. 1 is a schematic diagram of a handheld device according to an embodiment of the present invention.

Please refer to FIG. 1, which is a schematic diagram of a handheld device 10 according to an embodiment of the present invention. The handheld device 10 includes a base 100, a handgrip 110, a gripping element 150, an inertia sensor 120, a processing unit 130 and an actuator 140. The base 100 forms a main body of the handheld device 10 to include the protrusive handgrip 110 and the embedded components 120, 130, 140. The handgrip 110 may be held by a user. While hand muscles of the user unintentionally shake, the handgrip 110 receives a vibration movement VR. The inertia sensor 120 is utilized for detecting an acceleration of the vibration movement VR to generate an acceleration signal AC. The processing unit 130 is utilized for determining whether or not to generate a cancellation decision Dc based on the acceleration signal AC. The actuator 140 is utilized for controlling movement of the gripping element 150 if the cancellation decision Dc is made, so as to counteract the acceleration. As a result, the gripping element 150 can be stabilized. The gripping element 150 is utilized for releasably connecting the handheld device 10 to an object 160, such as a spoon. Since the gripping element 150 is stabilized, food in the spoon can be steadily held.

In comparison with the prior art, the handheld device 10 does not apply relatively large forces to an affected limb of the user, and therefore the user no longer suffers from the discomfort or pain. Instead, the handheld device 10 detects the acceleration of the vibration movement VR to accordingly counteract the acceleration, such that the user may easily deliver the food via the handheld device 10 and are no longer troubled by the tremors. In addition, shape memory alloy (SMA) is not employed in the handheld device 10, which means the user does not need to worry that the handheld device 10 will malfunction due to metal fatigue.

In addition, to distinguish between intended and unintended motions, a band pass filter may be incorporated. Please refer to FIG. 2, which is a schematic diagram of a handheld device 20 according to an embodiment of the present invention. Since the handheld device 20 is derived from the handheld device 10, the identical components are labeled by the same symbols. The handheld device 20 further includes a band pass filter 200. The band pass filter 200 is utilized for passing frequency components of the acceleration signal AC within a frequency range and rejecting the other frequency components outside the frequency range since a frequency component above the frequency range may be a noise, and a frequency component below the frequency range may not be induced by human tremors. Preferably, the range is 2-24 Hz.

Figure 2:
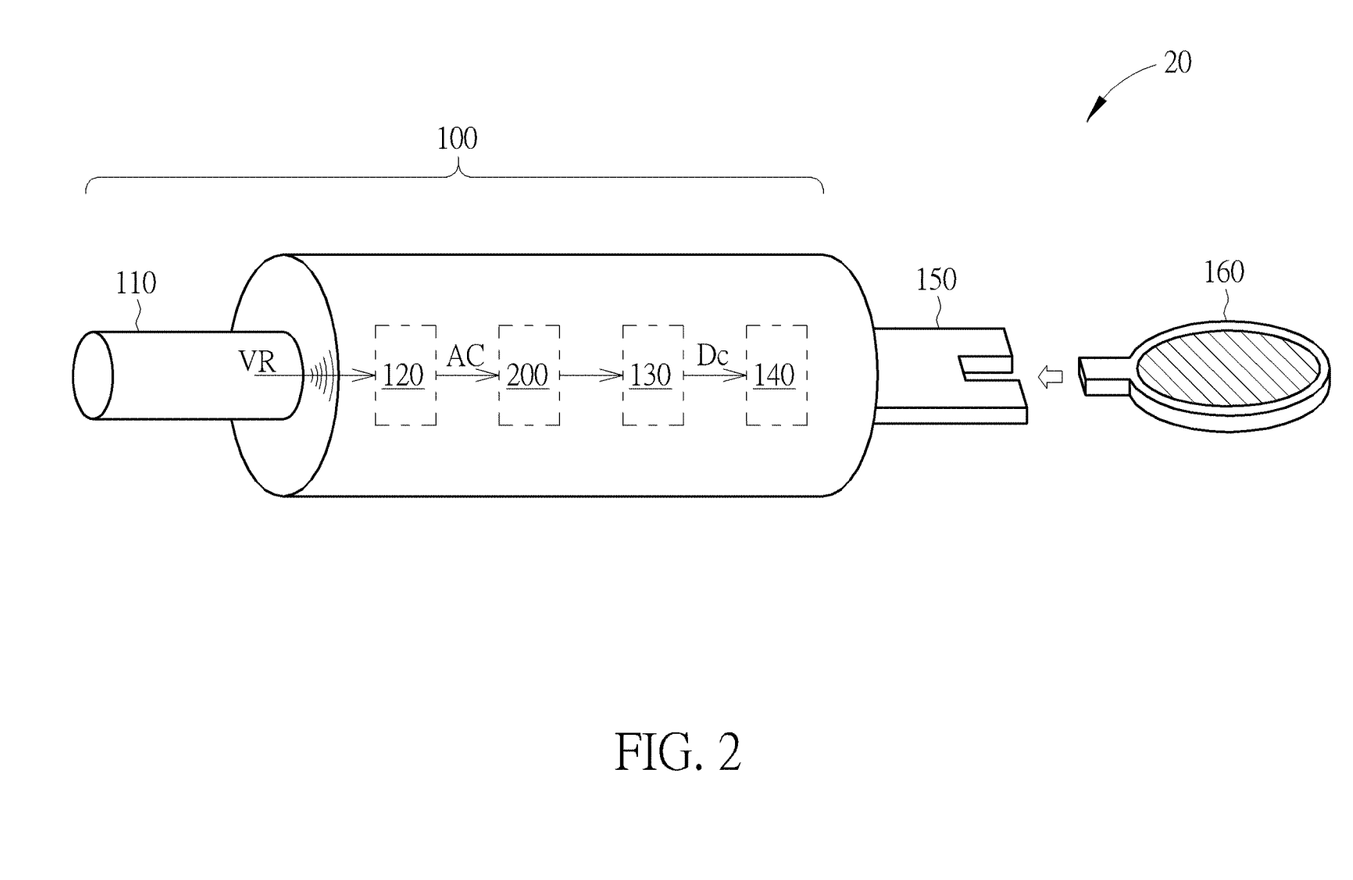
FIG. 2 is a schematic diagram of a handheld device according to an embodiment of the present invention.

Note that, the filtered acceleration signal still includes a gravity component induced by gravity. Therefore, the processing unit 130 is further utilizing for removing the gravity component from the acceleration signal AC to acquire the pure acceleration induced by the human tremors.

Figure 3A:
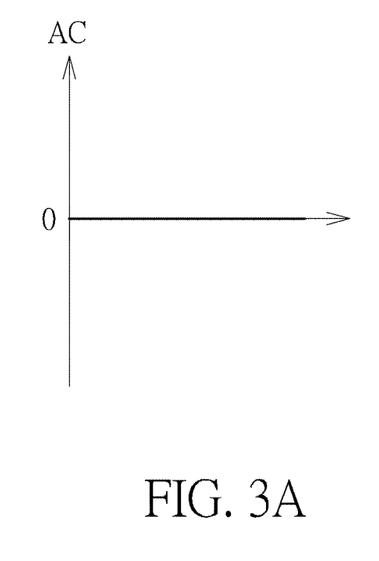
FIGS. 3A-3C are time-variant diagrams of the acceleration signal of the handheld devices in FIGS. 1 and 2.
Figure 3B:
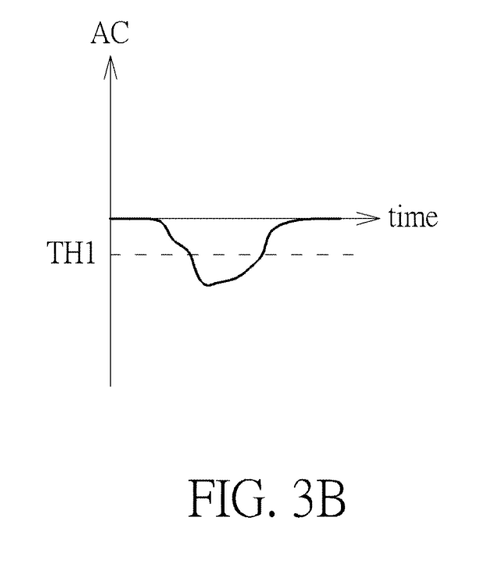
Figure 3C:
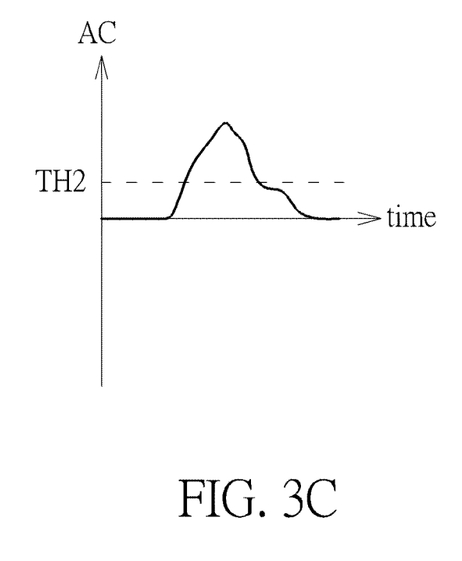

Specifically, please refer to FIG. 3A-3C, which are time-variant diagrams of the acceleration signal AC. In FIG. 3A, the base 100 is stable, and the acceleration signal AC is zero. In FIG. 3B, the base 100 is lowered down by the vibration movement VR, and a downward pulse appears in the acceleration signal AC. In FIG. 3C, the base 100 is lifted up by the vibration movement VR, and an upward pulse appears in the acceleration signal AC. That is, the processing unit 130 can determine whether to generate the cancellation decision Dc based on the downward or pulse. For example, if the base 100 is lowered by the vibration movement VR, the processing unit 130 generates the cancellation decision Dc based on the downward pulse, and the cancellation decision Dc indicates to the actuator 140 to lift up the gripping element 160 to counteract the acceleration. As a result, the gripping element 160 may remain a stable position. On the contrary, if the base 100 is lifted up by the vibration movement VR, the processing unit 130 generates the cancellation decision Dc based on the upward pulse, and the cancellation decision Dc indicates to the actuator 140 to lower down the gripping element 160 to counteract the acceleration.

Note that, preferably, the processing unit 130 does not respond to every pulse of the acceleration signal AC because insignificant pulses are meaningless noises. To do so, the processing unit 130 merely responds to a pulse of the acceleration signal AC which exceeds thresholds. For example, as illustrated in FIG. 3B, the processing unit 130 generates the cancellation decision Dc if the acceleration signal AC is less than a first threshold TH1. In another embodiment, as illustrated in FIG. 3C, the processing unit 130 generates the cancellation decision Dc if the acceleration signal AC is greater than a second threshold TH2.

Importantly, the present invention focuses on counteracting the acceleration caused by the tremors instead of completely dissolving the vibration movement VR. According to Newton's first law of motion, the food will not spill from the object 160 as long as acceleration of the object 160 remains zero. For example, if a tremor lowers down a handheld device of the prior art, the handheld device of the prior art will generate a motion in a direction opposite to the tremor. This kind of responsive mechanism cannot guarantee that acceleration of the food in the spoon is zero, and the food will spill from the spoon. In comparison, since the acceleration of the gripping element 150 is counteracted, the acceleration of the object 160 is minimized and damped to approach zero, and the food will remain at rest or continue to move at a constant velocity. In such a situation, the food can be safely delivered to a mouth of the user.

Figure 4:
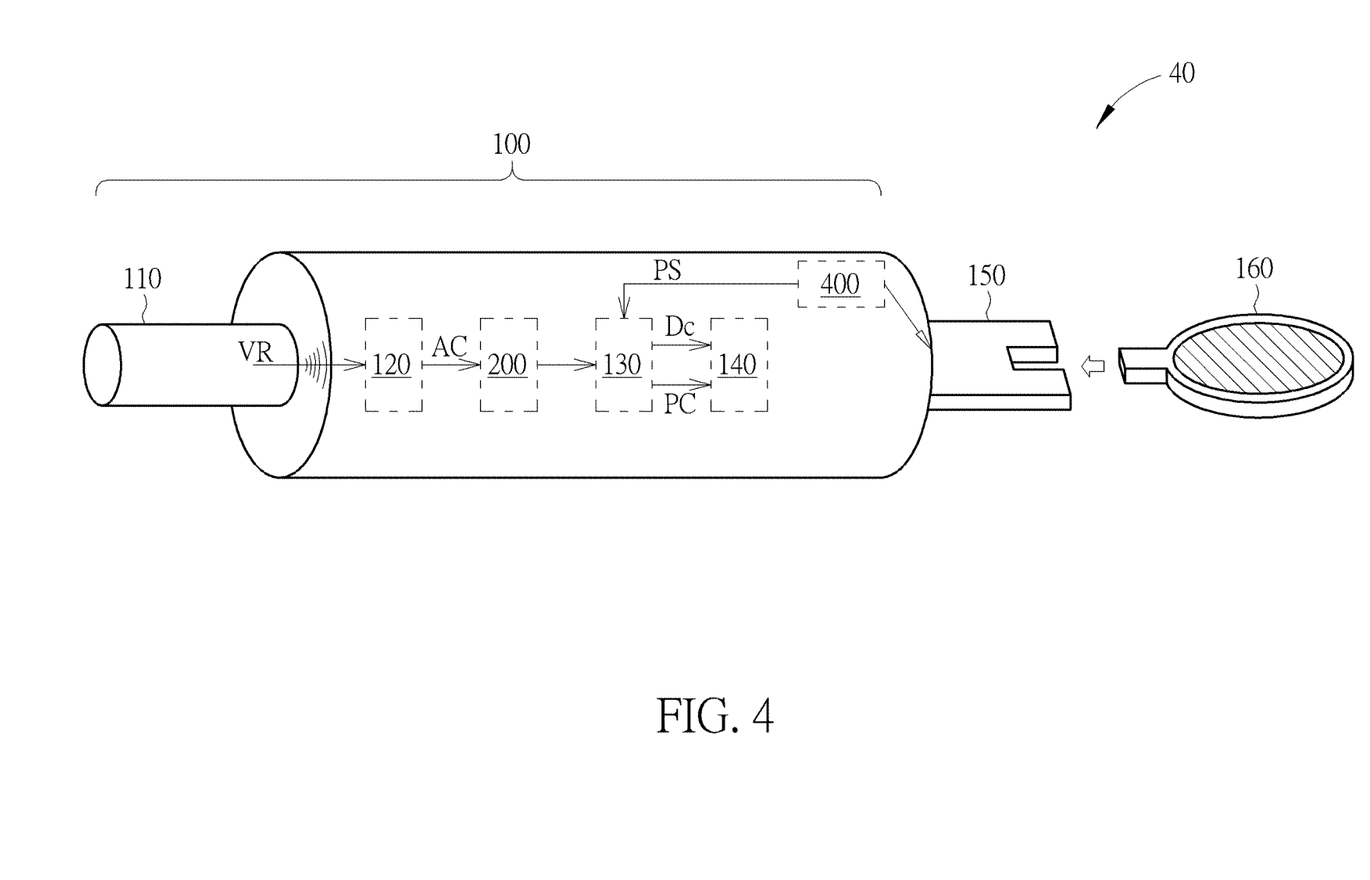
FIG. 4 is a schematic diagram of a handheld device according to an embodiment of the present invention.

Prior than acceleration check, a position calibration mechanism may be incorporated to improve preciseness of the acceleration check of the handheld devices 10, 20. Please refer to FIG. 4, which is a schematic diagram of the handheld device 40 according to an embodiment of the present invention. Since the handheld device 40 is derived from the handheld devices 10, 20, the identical components are labeled by the same symbols. The handheld device 40 further includes a position sensor 400. The position sensor 400 is utilized for detecting a position of the gripping element 150 to generate a position signal PS sent to the processing unit 130. The processing unit 130 determines whether the position is in a neutral position and accordingly generates a position calibration signal PC to instruct the actuator 140. If the position is in the neutral position, there is no need to calibrate the position of the gripping element 150. On the contrary, if the position is not in the neutral position, the position calibration signal PC instructs the actuator 140 to move down or up the gripping element 150 to reset the gripping element 150 back to a peripheral range centered at the neutral position.

Note that, the downward and upward movements illustrated in figures and described in the above embodiments are simplified cases. In practice, vibration movements induced by the tremors may be in any direction. The present invention may also be applied to those practical cases since base accelerations in directions other than downward and upward directions also can be counteracted. Accordingly, the handheld devices 10, 20, 40 may include more than one inertia sensors to detect accelerations in various directions, more than one position sensors to detect multiple positions of the gripping element 150, and more than one actuators to control multiple direction movements of the gripping element 150.

Figure 5:
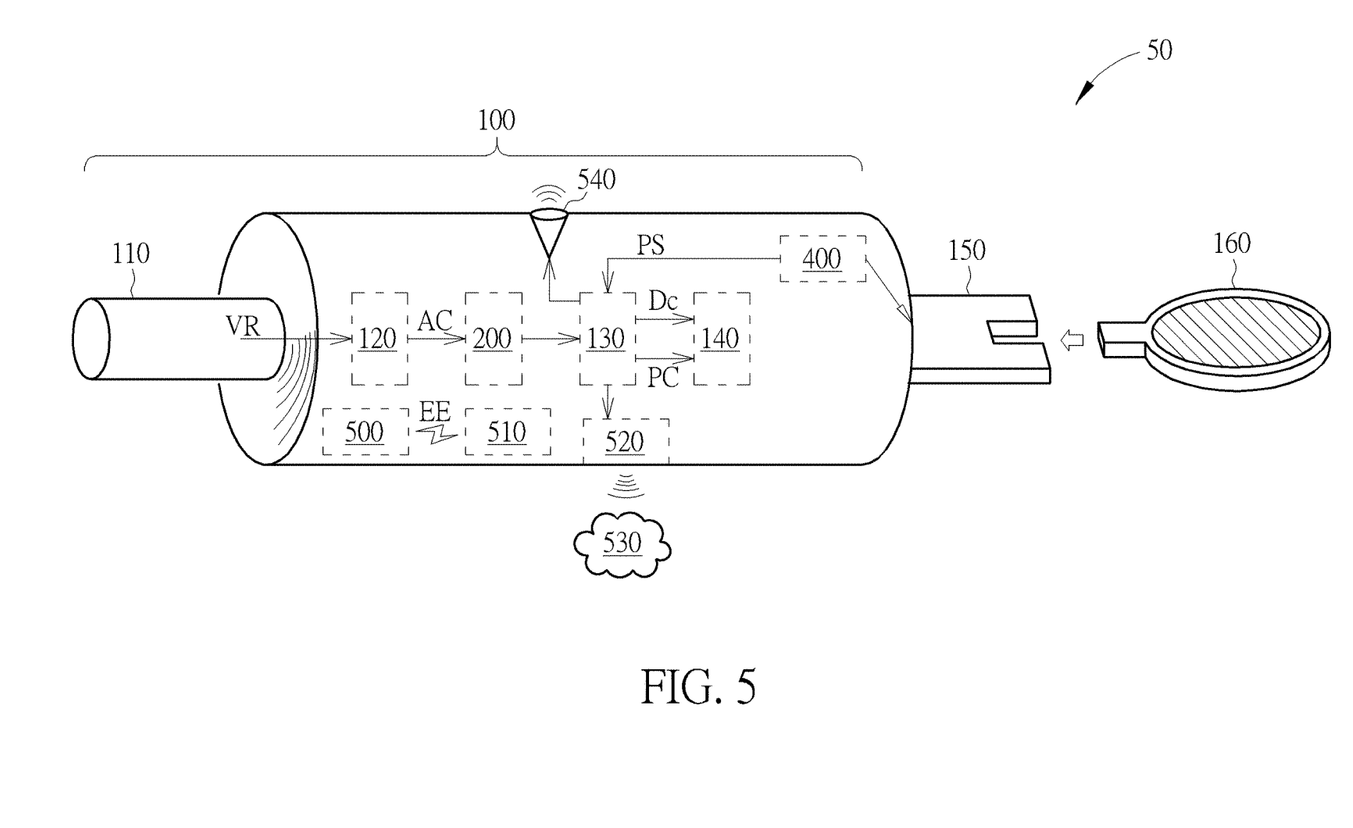
FIG. 5 is a schematic diagram of a handheld device according to an embodiment of the present invention.

Please refer to FIG. 5, which is a schematic diagram of a handheld device 50 according to an embodiment of the present invention. Since the handheld device 50 is derived from the handheld devices 10, 20, 40, the identical components are labeled by the same symbols. The handheld device 50 further includes a power converter 500, a battery 510, an interface module 520 and a micro acoustic speaker 540. The power converter 500 is utilized for converting a mechanical power of the vibration movement VR into an electrical power EE. The battery 510 is utilized for storing the electrical power EE. In addition, since history of the vibration movement VR and the acceleration signal AC are valuable in medical study, the interface module 520 may upload data of the vibration movement VR and the acceleration signal AC to at least one external device, such as a personal computer, a smart phone or a cloud server 530. The micro acoustic speaker 540 is utilized for noticing the user conditions of the handheld device 50 via sounds, such as charge percentage of the battery 510, position of the object 160, etc.

Furthermore, the processing unit 130 may determine whether there is a user holding the handgrip 110 based on the acceleration signal AC. If there is no user holding the handgrip 110 for a predetermined time period, the processing unit 130 can shut down the handheld devices 10, 20, 40, 50 to save power.

Figure 6:
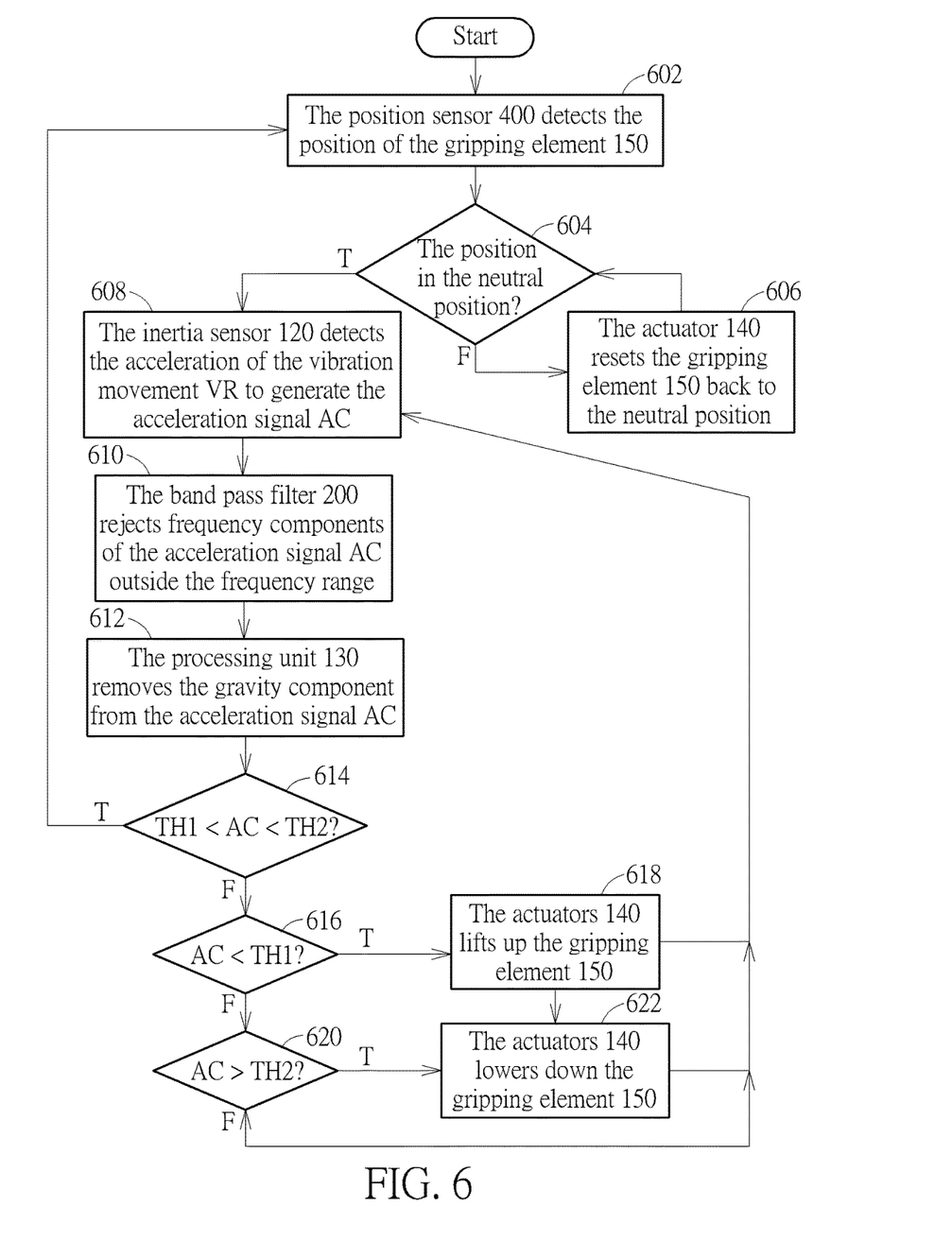
FIG. 6 is a flow chart illustrating operations of the handheld devices in FIGS. 1, 2, 4 and 5.

Operations of the handheld devices 10, 20, 40, 50 can be summarized into a process 60, as illustrated in FIG. 6. The process 60 includes the following steps:

Step 600: Start.

Step 602: The position sensor 400 detects the position of the gripping element 150.

Step 604: The processing unit 130 determines whether the position is in the neutral position. If true, go to Step 608; else go to Step 606.

Step 606: The actuator 140 resets the gripping element 150 back to the neutral position, and go to Step 604.

Step 608: The inertia sensor 120 detects the acceleration of the vibration movement VR to generate the acceleration signal AC.

Step 610: The band pass filter 200 rejects frequency components of the acceleration signal AC outside the frequency range.

Step 612: The processing unit 130 removes the gravity component from the acceleration signal AC.

Step 614: If the acceleration signal AC is between the first threshold TH1 and the second threshold TH2, go to Step 602; else, go to Step 616.

Step 616: If the acceleration signal AC is less than the first threshold TH1, go to Step 618; else, go to Step 620.

Step 618: The actuators 140 lifts up the gripping element 150, and go to Step 608.

Step 620: If the acceleration signal AC is greater than the second threshold TH2, go to Step 622; else, go to Step 608.

Step 622: The actuators 140 lowers down the gripping element 150, and go to Step 608.

Details of the process 60 are described in the above, and are not further narrated again herein.

To sum up, to minimize discomfort and pain of an unintentional-muscle-moving patient, the present invention counteracts the acceleration of the tremors. As long as the unintentional acceleration is balanced, the patient can engage daily activities with less inconvenience.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A handheld device, comprising:
   a base comprising a handgrip, for receiving a vibration movement;
   a gripping element linked to the base for releasably connecting the handheld device to an object;
   at least one inertia sensor, for detecting an acceleration of the vibration movement to generate an acceleration signal;
   a band pass filter, for passing the acceleration signal within a frequency range and filtering out the acceleration signal outside the frequency range;
   a processing unit, for generating a cancellation decision if the acceleration signal within the frequency range is less than a first acceleration threshold or greater than a second acceleration threshold;
   at least one actuator, for controlling movement of the gripping element according to the cancellation decision such that the acceleration is counteracted, lifting up the gripping element only if the acceleration signal within the frequency range is less than the first acceleration threshold, and lowering down the gripping element only if the acceleration signal within the frequency range is greater than the second acceleration threshold.

2. The handheld device of claim 1, wherein the processing unit is further utilized for removing a gravity component from the acceleration signal.

3. The handheld device of claim 1, further comprising at least one position sensor for detecting a position of the gripping element to generate a position signal.

4. The handheld device of claim 3, wherein the processing unit is further utilized for determining whether the position is in a neutral position according to the position signal to generate a position calibration signal.

5. The handheld device of claim 4, wherein the position calibration signal is utilized for instructing to the actuator to reset the gripping element back to the neutral position.

6. The handheld device of claim 1, further comprising:
   a power converter, for converting a mechanical power of the vibration movement into an electrical power;
   a battery, electrically coupled to the power converter, for storing the electrical power; and
   a speaker, coupled to the processing unit, for broadcasting an acoustic notice of a condition of the handheld device.

7. The handheld device of claim 1, further comprising:
   an interface module, electrically coupled to the processing unit, for uploading data of the vibration movement and the acceleration signal to at least one external device.

8. The handheld device of claim 1, wherein the processing unit is further utilized for determining whether the handgrip is held according to the acceleration signal and shutting down the handheld device if the handgrip is not held for a time period.

* * * * *